United States Patent [19]

Allred, III et al.

[11] Patent Number: 4,787,369

[45] Date of Patent: Nov. 29, 1988

[54] FORCE RELIEVING, FORCE LIMITING SELF-ADJUSTING STEERING FOR BORESCOPE OR ENDOSCOPE

[75] Inventors: Jimmie B. Allred, III, Skaneateles; Allan I. Krauter, Syracuse, both of N.Y.

[73] Assignee: Welch Allyn, Inc., Skaneateles Falls, N.Y.

[21] Appl. No.: 85,347

[22] Filed: Aug. 14, 1987

[51] Int. Cl.$^4$ .............................................. A61B 1/00
[52] U.S. Cl. .......................................... 128/4; 356/241
[58] Field of Search ........................... 128/4, 6, 3, 5, 7; 138/119, 120; 350/96.26; 356/241

[56] References Cited

U.S. PATENT DOCUMENTS

| Re. 31,289 | 6/1983 | Moore et al. | 128/6 |
|---|---|---|---|
| Re. 31,290 | 6/1983 | Moore et al. | 128/6 |
| 3,060,972 | 10/1962 | Sheldon | 138/120 |
| 3,190,286 | 6/1965 | Stokes | 128/6 |
| 3,557,780 | 1/1971 | Sato | 128/4 |
| 3,583,393 | 6/1971 | Takahashi | 128/4 |
| 3,610,231 | 10/1971 | Takahashi | 128/6 |
| 3,669,098 | 6/1972 | Takahashi | 128/6 |
| 3,739,770 | 6/1973 | Mori | 128/6 |
| 3,799,151 | 3/1974 | Fukaumi et al. | 128/6 |
| 4,108,221 | 8/1978 | Freimuth et al. | 92/13.7 X |
| 4,347,837 | 9/1982 | Hosono | 128/6 |
| 4,700,693 | 10/1987 | Lia et al. | 128/4 |

Primary Examiner—William H. Grieb
Attorney, Agent, or Firm—Wall and Roehrig

[57] ABSTRACT

A self-adjusting mechanism ensures that the collective force on the steering cables of an endoscope or borescope is limited or relieved when a predetermined force is reached. The mechanism includes a frame, a slider that moves on the frame and restrains the proximal ends of the steering cable sheaths, and springs that bias the slider distally. The springs can be preloaded by employing a stop member to limit the distal movement of the slider.

7 Claims, 3 Drawing Sheets

FORCE RELIEVING, FORCE LIMITING SELF-ADJUSTING STEERING FOR BORESCOPE OR ENDOSCOPE

BACKGROUND OF THE INVENTION

This invention relates to a controllably bendable tube assembly, especially a borescope or endoscope of the type having a cable-actuated hollow steering section.

An endoscope is generally characterized as an elongated flexible tube, i.e. an insertion tube, with a viewing head at its distal or forward end, and a control section at its proximal end for controlling or steering the distal end. In such an endoscope, a bendable tube steering section is situated at the distal end adjacent to the viewing head. One or two pairs of control cables extend through the bendable tube section and the remainder of the insertion tube and connect with a steering control mechanism in the control section. One or both pairs of these cables are differentially displaced for bending the steering section to facilitate the inspection of an object.

An endoscope is typically inserted into a body cavity of a patient for visual investigation of tissues within the cavity. For example, an endoscope can be inserted into the colon, stomach, or lung of a patient. Because the esophagus, bronchii, and colon are narrow, tortuous passageways, the steering section must be bent rather precisely, and as close to the viewing head as possible, in order to obtain the necessary penetration without damaging the patient's tissues. It is most desirable that both the cable tension be limited and that cable slack be minimized.

A borescope is a similar device, but intended for visual inspection of a mechanical assembly, such as a jet engine or turbine, where it would be difficult or impossible otherwise to the assembly's internal elements. The borescope needs to be insertable into narrow tortuous passageways, and must observe similar steering and bending considerations.

A number of types of steering mechanisms are known. For example, helically coiled strips are employed in endoscopes or borescopes as described in U.S. Pat. Nos. 3,610,231 and 3,739,770. Steering sections formed of thin-walled cylindrical segments or bands that are joined by means of pins or bifurcations, or other similar articulations such that the segments are rockable on one another, are described in U.S. Pat. Nos. 3,583,393; 3,669,098; 3,799,151; and 4,347,837. U.S. Pat. No. 3,557,780 describes an endoscope steering section formed of two flexure portions, with two sets of control wires. Stays or flexible backbone members of various lengths control the degree of curving and the location of the curvature on the steering section.

An endoscope described in the U.S. Pat. No. 3,799,151, has cylindrical segments articulated in one plane or another plane as required to select the amount and direction of bending of the endoscope steering section.

For those steering sections that are bendable in two planes, a significant amount of cable slack is typically included so that the steering cables for one plane do not bind when the steering section is bent in the other plane. Some cable slack is also included to accommodate cable tightening due to coiling and bending of the insertion tube through which the steering cables pass. The endoscopes and borescopes are usually coiled for shipping and storage, but are generally straight when in use. This coiling can place large stresses on the cables, leading to cable failure.

In a steerable endoscope or borescope, opposing steering cables are displaced to deflect its distal tip. These cables are differentially displaced. That is, as one cable is pulled away from the bending section, the other moves towards the bending section. However, the motion of the one cable is not normally the exact opposite of the motion of the other. Coiling of the insertion tube can result in the tensioning, at the same time, of both cables of an opposed pair. This tensioning produces friction and high forces that can damage the steering section or cables, leading to early failure. Adding cable play or slack can alleviate this problem, but can create other problems, such as imprecise steering. Moreover, large steering knob movements are then required for deflection of the endoscope or borescope tip.

OBJECTS AND SUMMARY OF THE INVENTION

Accordingly, it is an object of this invention to provide a borescope or endoscope which avoids the drawbacks of the prior art.

It is a more specific object of this invention to provide a cable bendable borescope or endoscope that has a minimal amount of slack and which is easy to deflect, even when the insertion tube section is coiled or the steering section is fully deflected in another plane.

It is another object of this invention to minimize or eliminate the need for cable adjustment in endoscopes or borescopes.

It is a further object of this invention to limit or minimize the collective or total force on the pair of cables, or to relieve cable forces when they exceed a threshold.

It is a still further object of this invention to provide a force-limiting/force-relieving mechanism which accomplishes the above objects, but which is simple in design and sufficiently compact to be housed in the control section housing.

As aforesaid, the ideal self-adjusting mechanism should ensure that the collective force applied to the steering cables of an opposed pair does not exceed a predetermined maximum. To this end, the self-adjusting mechanism has a frame fixedly mounted within the control section and including a track that is oriented axially, i.e., along the direction of cable motion. A slider is disposed to slide axially along the frame, i.e., in the direction of cable motion.

The slider is freely movable along the frame and is not restrained for axial motion except by proximally directed forces exerted by the cable sheaths, and by distally directed force from a spring (or set of springs) acting between the frame and the slider.

In a force-limiting self-adjusting mechanism, the spring force adjusts to equal the total or collective force imposed on the slider by the cable sheaths. In a force-relieving self-adjusting mechanism, a stop or other preloading means preloads the spring or springs and the slider does not move until the cable sheath forces exceed the preload spring force.

In one preferred embodiment, the frame includes two rods arranged parallel to the steering cables, with the slider being a block with axial bores that the two rods fit through. First and second cable passages in the slider receive the first and second cable sheaths. There are adjusting nuts on the sheaths at their proximal ends which engage the slider to limit relative motion of the cable sheaths proximally relative to the slider. If there is force on both the cables, the sheaths, by means of the adjusting nuts, will push the slider proximally, opposing the distally directed force of a reset or force-control spring that acts between the slider and the frame. The mechanism takes up cable slack when slack is not required, and translates a maximum amount of cable motion into steering deflection.

The above and many other objects, features, and advantages of this invention will be more fully understood from the ensuing detailed description of some exemplary preferred embodiments of the invention, which description should be read in connection with the accompanying drawing.

DETAILED DESCRIPTION OF THE PREFERRED EMBODIMENTS

Figure 1:
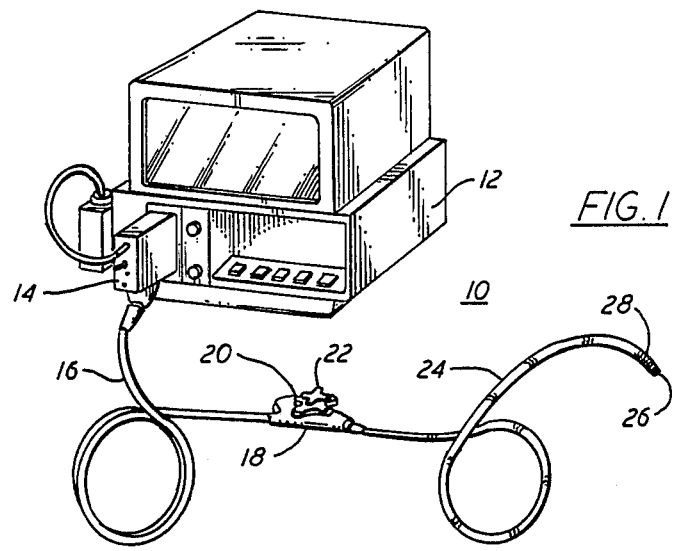
FIG. 1 is a perspective view of a video endoscope of the type which can employ the self-adjusting steering mechanism of this invention.
Figure 2:
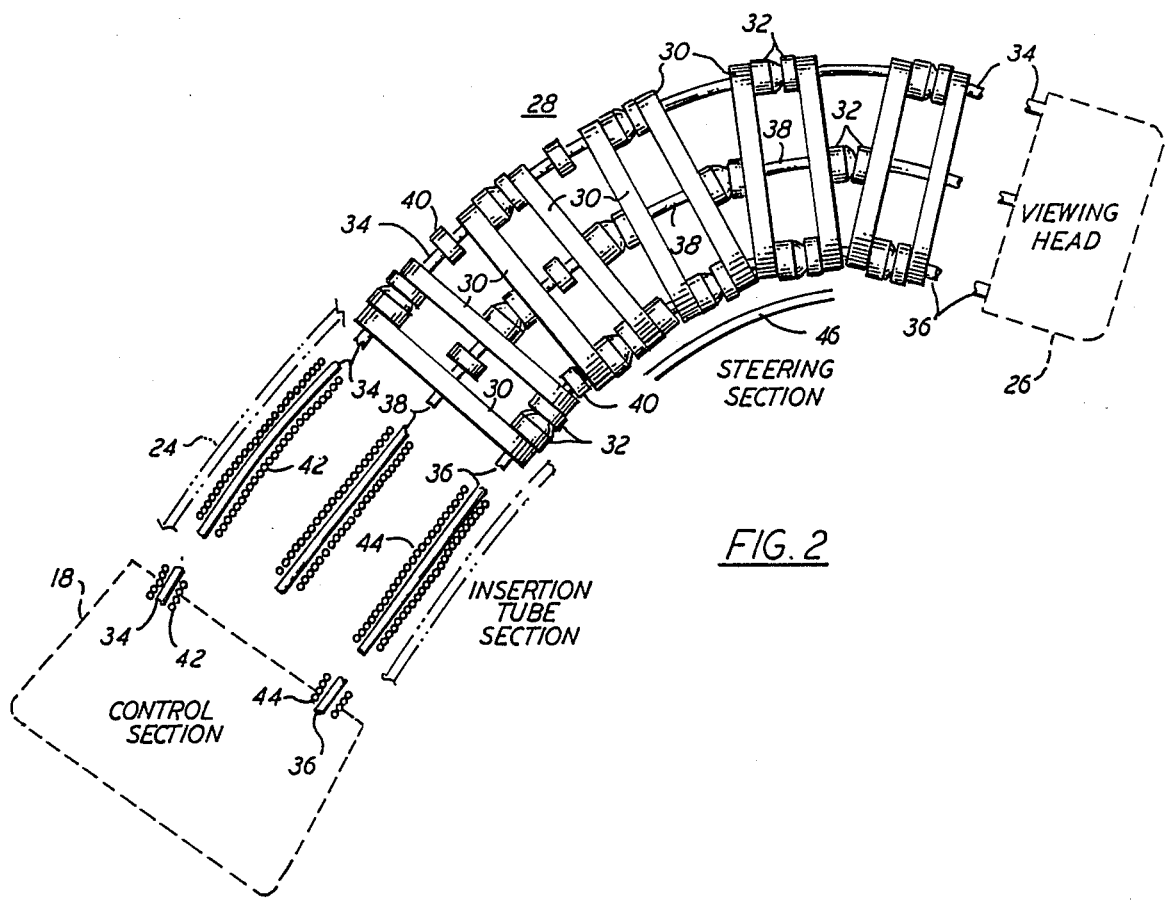
FIG. 2 is a schematic view, partly cut away, of a cable-type steering section of the endoscope of FIG. 1.

With reference to the drawing, FIG. 1 shows a video endoscope system 10, having a video monitor and console 12, with a connector adaptor 14 that connects the console 12 through an umbilical 16 to an endoscope control unit 18. The control unit 18 has a pair of steering knobs 20 and 22 for deflecting the endoscope tip in the upwards-downwards direction and in the left-right direction, respectively. An elongated flexible insertion tube 24 extends from the control unit and has at its tip a viewing head 26 that contains illuminating and video pick-up devices. Just to the proximal side of the viewing head 26 is a steering section 28 of the cable-actuated type of which an example is shown in FIG. 2. Many such steering mechanisms exist, as described in the patents identified earlier. Endoscopes of this general design are described e.g., in U.S. Pat. Nos. Re 31,289 and Re 31,290 each of June 28, 1983.

Borescopes are of similar design, but typically with longer insertion tubes.

FIG. 2 illustrates a steering section 28 of the type described in commonly assigned patent application Nos. 806,667, and 07/078,713 now U.S. Pat. No. 4,700,693 .

Other articulated cable-type steering mechanisms are described in U.S. Pat. Nos. 3,610,231; 3,739,770; 3,583,393; 3,669,098; 3,799,151; 4,347,837; 3,557,780; 3,060,972; 4,108,221; and 3,190,286.

In FIG. 2, the steering section 28 is formed of a stack of apertured washers 30, sometimes called vertebrae or discs, which are separated by an arrangement of spacer beads 32. To effect upward-downward deflection of the viewing head 26, an upper steering cable 34 and a lower steering cable 36 penetrate through opposite sides of the washers 30 and through the associated spacer beads 32, and are affixed onto the viewing head 26. These cables 34 and 36 extend back through the insertion tube 24 to the control section 18. Also shown is another cable 38 (its opposing associated cable is obscured in this view) for controlling right-to-left steering. Limiter beads 40 are disposed on the cable at selected locations to limit the amount of bending of the steering section, especially at the proximal end thereof.

Within the insertion tube 24, the cables 34 and 36 run through cable sheaths 42 and 44 respectively. These sheaths are flexible but resist axial compression. Thus, the cable sheaths 42 and 44 provide reaction forces for the forces on the cables 34 and 36, so that any cable motion is transferred from the control section 18 to the steering section 28.

The flexible insertion tube 24 terminates at the steering section 28. A flexible outer covering 46 covers the steering section 28 and is attached to the insertion tube 24 and to the viewing head 26. The cable sheaths 42 and 44 are anchored at the proximal side of the steering section 28 and their proximal ends extend into the control section 18. The cables 34, 36 are themselves anchored in the viewing head 26, and the proximal ends thereof are connected to a windlass arrangement (not shown) in the control section 18.

Figure 3:
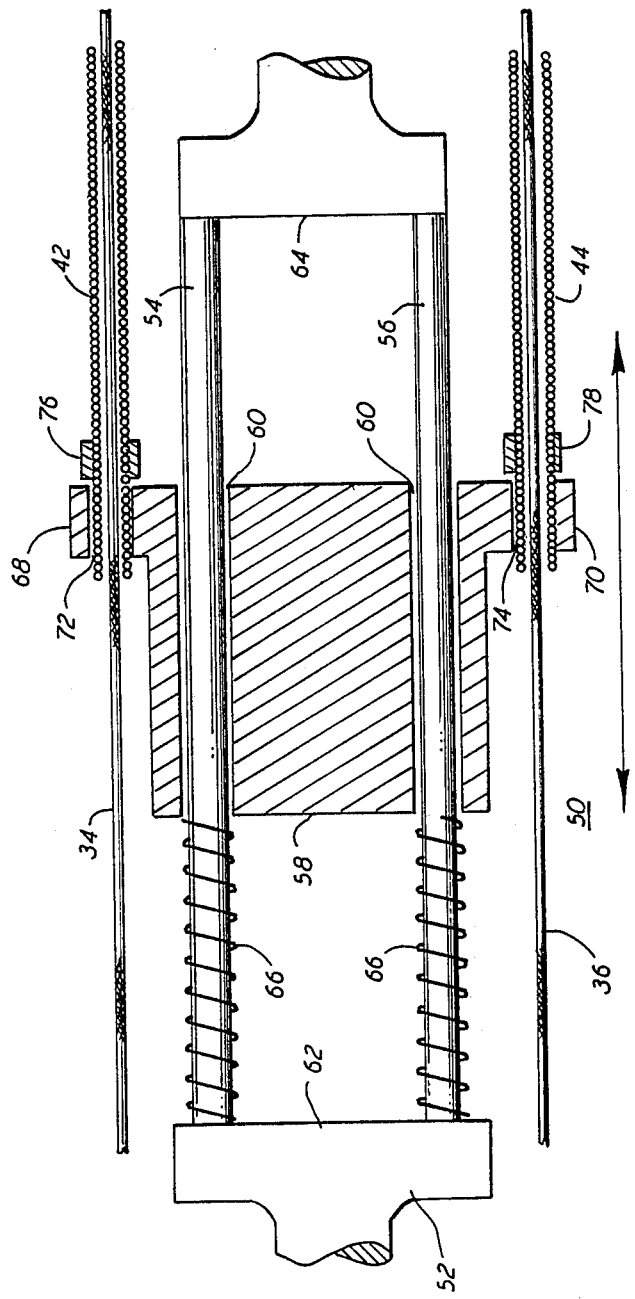
FIG. 3 is a schematic sectional view of a force-limiting self-adjusting mechanism according to a first embodiment of the invention.

As shown in FIG. 3, a force-limiting self-adjusting mechanism 50 according to one preferred embodiment of this invention has a frame member 52 affixed inside the housing of the steering section 18. This frame member 52 is comprised of upper and lower rods 54 and 56 which extend in the axial direction, i.e., parallel to the cables 34 and 36. A block-type slider 58 is fitted onto the frame member 52 to slide on the rods 54,56 and to this end it has a pair of axial bores 60 through which the upper and lower rods 54 and 56 respectively pass. The rods 54,56 form a longitudinal track on which the slider 58 is movable proximally and distally.

The frame 52 has a proximal member 62 and a distal member 64 between which the rods 54,56 are supported. The slider 58 is generally free to travel the rods 54,56, except as restrained by forces imparted by the cable sheaths 42,44 and by coil type reset force-control springs 66 which are disposed over the rods 54,56 between the slider 58 and the frame proximal member 62.

The slider 58 has a pair of lateral projections 68,70, each of which has a passage 72,74 therethrough to receive a respective one of the cables 34,36 and its associated sheath 42,44. Each cable sheath 42,44 has an adjusting nut 76,78 near its proximal end to serve as a stop, i.e., to limit relative motion of the cable sheaths 42,44 and the slider towards one another.

The mechanism 50 attempts to maintain a specified total force on the two cables 34,36 through the movable, preloaded slider 58. The force-control springs 66 are preloaded by means of the pushing forces on the cable sheaths 42,44. Here, the cable sheaths 42,44 are free in the passages 72,74, so the adjusting nuts 76,78 push the slider 58 proximally. The forces of the two nuts 76,78 together are equal and opposite to the forces of the two force-control springs 66.

Operation of the mechanism 50 is generally as follows, with the example describing steering the endoscope or borescope steering section 28 from a straight to an upwardly bent condition. Initially, both cables 34,36 and both sheaths 42,44 each have half the total preload force of the force-control reset springs 66. As the upper cable is withdrawn (i.e., moved proximally) the force on the upper cable 34 remains constant provided that no lateral loads are applied to the steering section 28. Friction and cable bending resistance are disregarded here. The force on the lower cable 36 remains constant also. If a load is encountered by the steering section 28, a higher force will be encountered by the cables 34,36. The force on the upper cable 34 will increase if a load is encountered when the upper cable is moved proximally, to equal the increased load. The force on the lower cable 36 will decrease to keep the total force on the slider 58 a constant. If greater loads are encountered when the upper cable 34 is moved proximally so that more force is required than is provided by the force-control reset springs 66, the force on the lower cable will reduce to zero and the slider 58 will move proximally, compressing the springs 66 and increasing their force. The forces that can be applied to the steering section 28 are limited by the spring force of the force control reset springs 66.

Alternatively, to the slider arrangement here, a pivoting member and a torsion spring could, for example, be employed to achieve the same ends by functioning as a movable member and resilient biasing means.

This mechanism 50 has other advantages. Because the steering cable sheaths 42 and 44 are always loaded, steering slack or play is never present. The spring force of the force control reset springs 66 automatically compensates cable stretch by distal movement of the slider 58. Moreover, the coiling of the insertion tube 24 is also compensated; the coiling simply causes the slider to move proximally by the amount the cables would have been stretched (or slack would have been reduced) in a conventional endoscope or borescope. Motion of the slider 58 increases force on the cables 34,36 only to the extent that the force control reset springs 66 are compressed slightly beyond their initial, or preload point.

Figure 4:
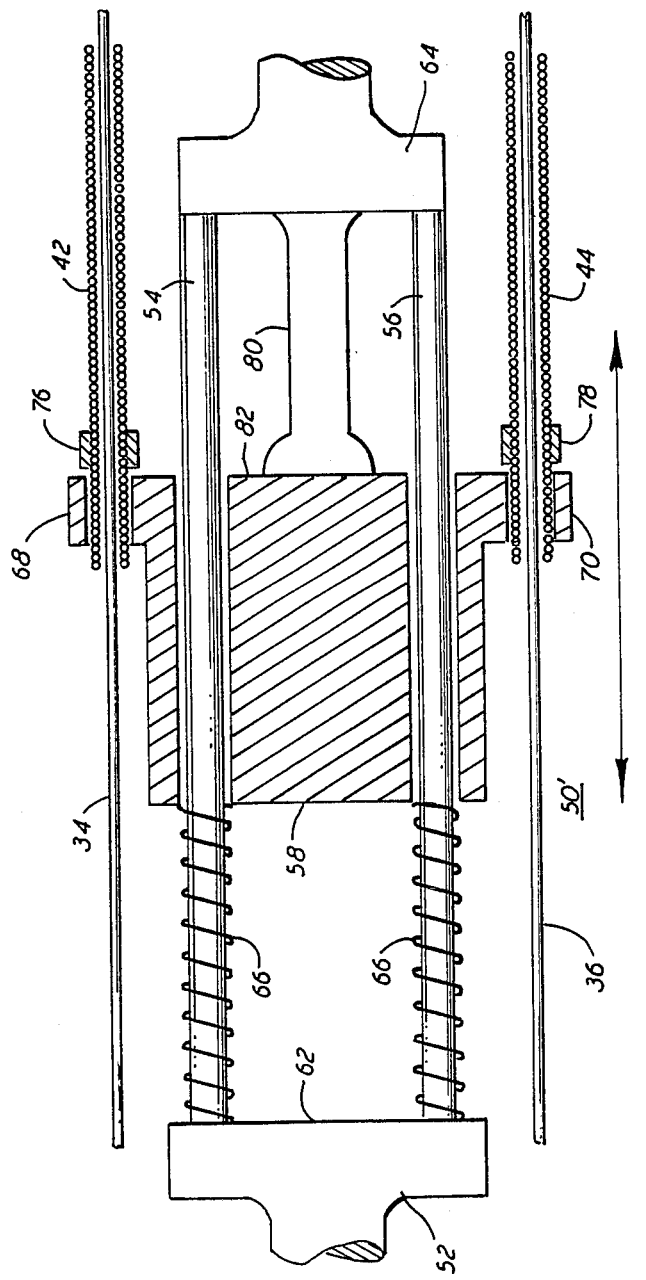
FIG. 4 is a schematic sectional view of a force-relieving self-adjusting mechanism according to a second embodiment of the invention.

A second embodiment of this invention, namely a force-relieving self-adjusting mechanism 50' is shown in FIG. 4. This has structure quite similar to that of the force-limiting mechanism 50 of FIG. 3, and common elements are identified with the same reference numbers. A detailed description of the elements common to both embodiments is omitted.

In this embodiment, the springs 66 are preloaded by means of a stop member 80 that extends proximally from the frame distal member 64 and abuts a distal face 82 of the slider 58. The springs 66 are preloaded such that the spring force exceeds the steering forces that are normally encountered by the cables 34 and 36.

Operation of the mechanism 50', up to a point, is identical to that of conventional endoscopes. That is, steering play or slack is provided between the steering controls and the steering cables 34,36, up to an amount that is considered typical. This slack is reduced as the insertion tube 24 is coiled, e.g., for shipment or storage. When all of the cable slack has been used up, additional coiling activates the mechanism 50'.

The total compressive force on the cable sheaths 42,44, (which is equal to the total tension force on the cables 34,36) increases until it equals the preload force imposed by the stop member 80 on the springs 66. Then, additional compressive force moves the slider 58 proximally. Further coiling moves the slider 58 additionally until the compressive force on the sheaths 42,44 is balanced by the force on the springs 66. Uncoiling of the insertion tube 24 moves the slider distally until it contacts the stop member 80. Prior to slider-stop member contact, the cable forces and the forces of the force control reset springs 66 remain equal. After the insertion tube 24 is uncoiled to the point where slider-stop member contact is made, slack is created in at least one cable 34 or 36.

While the invention has been described in detail with reference to preferred embodiments, it should be recognized that the invention is not limited only to those embodiments, but rather that many modifications and variations thereof would be apparent to those of skill in the art without departing from the scope and spirit of tis invention, as defined in the appended claims.

What is claimed is:

1. Self-adjusting steering mechanism for endoscopes of the type having a flexible insertion tube, a distal steering section, at least one pair of steering cables that are enclosed in respective cable sheaths for controlling bending of said steering section, a control housing at a proximal end of the insertion tube, and means in said control housing for displacing said control cables relative to said sheaths; the mechanism comprising a frame fixed in said control housing;

a movable member supported on said frame and disposed for motion generally proximally-distally, the movable member including passages for receiving the proximal ends of said cable sheaths, said cable sheaths each having stop means for limiting proximal motion of said cable sheaths relative to said movable member; and force-control spring means biasing said movable member distally on said track.

2. The self-adjusting steering mechanism of claim 1 in which said movable member includes a slider and said from include an axially-disposed longitudinal track supporting the slider for axial motion therealong.

3. The self-adjusting steering mechanism of claim 2 in which said slider is freely slidable on said track and is restrained only by forces of said cable sheaths and said spring means.

4. The self-adjusting steering mechanism of claim 2 in which said track includes a pair of longitudinal rods and said slider has longitudinal passages through which said rods pass.

5. The self-adjusting steering mechanism of claim 4 in which said spring means include respective coil springs disposed over said rods.

6. The self-adjusting steering mechanism of claim 1, further comprising preloading means for imposing a preload force on said spring means, such that said movable member is held against proximal motion on said frame until the forces on said pair of cable sheaths exceed said preload force.

7. The self-adjusting steering mechanism of claim 6, wherein said preloading means includes a stop member on said frame limiting travel of the movable member in the distal direction to a predetermined position on said track, the predetermined position being selected so that said preload force is produced by the spring means at that position.

* * * * *

UNITED STATES PATENT AND TRADEMARK OFFICE
CERTIFICATE OF CORRECTION

PATENT NO. : 4,787,369

DATED : November 29, 1988

INVENTOR(S) : Jimmie B. Allred, III et al.

It is certified that error appears in the above-identified patent and that said Letters Patent is hereby corrected as shown below:

Claim 2, line 34, "from include" should read "frame includes".

Signed and Sealed this

Twenty-fifth Day of July, 1989

Attest:

DONALD J. QUIGG

Attesting Officer

Commissioner of Patents and Trademarks